United States Patent [19]

Graindorge et al.

[11] Patent Number: 5,550,267

[45] Date of Patent: Aug. 27, 1996

[54] PROCESS FOR THE SYNTHESIS OF HALOALKYLFERROCENES

[75] Inventors: Hervé Graindorge, Vert le Petit; Jean-Claude Mondet, Vert le Grand; Charles-Henry Vincent, Precy sur Oise, all of France

[73] Assignee: Societe Nationale Des Poudres Et Explosifs, Paris, France

[21] Appl. No.: 470,966

[22] Filed: Jun. 6, 1995

[30] Foreign Application Priority Data

Jun. 14, 1994 [FR] France .................. 94 07223

[51] Int. Cl.$^6$ .................. C07F 15/02; C07F 17/02
[52] U.S. Cl. .................. 556/144
[58] Field of Search .................. 556/144

[56] References Cited

U.S. PATENT DOCUMENTS

| | | | |
|---|---|---|---|
| 3,960,911 | 1/1976 | Suschitzky et al. | 556/144 |
| 4,647,628 | 3/1987 | Gautier et al. | |
| 4,668,313 | 5/1987 | Gautier et al. | |
| 5,110,964 | 5/1992 | Hiroi et al. | 556/144 X |
| 5,190,671 | 3/1993 | Caubere et al. | |
| 5,214,175 | 5/1993 | Gautier et al. | |

FOREIGN PATENT DOCUMENTS

| | | |
|---|---|---|
| 2567895 | 1/1984 | France . |
| 2667318 | 4/1992 | France . |
| 2667600 | 4/1992 | France . |

OTHER PUBLICATIONS

Schlogl, et al: "Darstellung von Alkylferrocenen aus Acylferrocenen durch Reduktion mit Lithiumalanat–Aluminiumchlorid": (Monatschefte für Chemie, Bd. 92/4) pp. 921–926, Jun. 1961.

Chemical Abstracts, vol. 081, No. 3, Abstract No. 013631d, Jul. 22, 1974.

*Primary Examiner*—Paul F. Shaver
*Attorney, Agent, or Firm*—Cushman Darby & Cushman, L.L.P.

[57] ABSTRACT

The present invention relates to a process for the synthesis of haloalkylferrocenes, comprising a first stage of reaction, in the presence of $AlCl_3$ as catalyst and in organic solvent medium, of a carboxylic acid halide or anhydride with ferrocene or an alkylferrocene.

After this stage, without prior isolation of the intermediate compound, a metal hydride is added to the reaction mixture.

The haloalkylferrocenes are particularly useful as intermediates in the synthesis of combustion catalysts for propellants.

10 Claims, No Drawings

PROCESS FOR THE SYNTHESIS OF HALOALKYLFERROCENES

The present invention relates to a new process for the synthesis of haloalkylferrocenes.

Haloalkylferrocenes are particularly useful as intermediates in the synthesis of ferrocene combustion catalysts for propellants, such as the ethylenically unsaturated polymers containing silylferrocene groups described in French Patent FR 2,567,895. The silylferrocene grafts of these polymers are generally obtained by reaction of the magnesium derivative of the abovementioned haloalkylferrocenes with a dialkylhalosilane and the production of silylferrocene grafts with a high yield and a high purity is essential in order finally to obtain, at a not exorbitant cost, a silylferrocene polymer of satisfactory quality for it to be used in propellants.

These constraints make it necessary to produce haloalkylferrocenes of high purity, with a high yield, according to a process which is as simple and inexpensive as possible.

It is known to produce haloalkylferrocenes from ferrocene in two reaction stages.

The first reaction stage consists in synthesizing a haloalkanoylferrocene compound by a reaction of "Friedel-Crafts" type, in the presence of aluminum chloride as catalyst and in organic solvent medium, by reaction of ferrocene with a carboxylic acid halide or anhydride. This haloalkanoylferrocene intermediate is isolated from the reaction mixture and purified.

The second reaction stage consists in reducing the abovementioned haloalkanoylferrocene derivative, chemically or by catalytic hydrogenation, to the corresponding haloalkylferrocene derivative. The chief difficulty consists in reducing the ketone functional group without reducing the halogen functional group.

Generally, this access route to haloalkylferrocenes according to the two abovementioned reaction stages is very restricted, in particular as a result of significant difficulties, and of the cost which this entails, in purifying the crude products obtained on completion of each of these two stages.

These purifications are necessary as a result of the presence, in relatively large amounts, of ferrocene and 1,1'-di(haloalkanoyl)ferrocene as impurities in the crude intermediate haloalkanoylferrocene. In fact, on the one hand, the residual ferrocene has a tendency to sublime and then to deposit on all the cold walls (traps, pipework, and the like) during the subsequent stages and, on the other hand, the presence of 1,1'-di(haloalkanoyl) ferrocene leads to ferrocenic polymers of poor quality, as a result of its difunctionality which leads to inopportune crosslinking.

French Patent FR 2,667,318 describes a process for the synthesis of monohaloalkylferrocenes by catalytic hydrogenation in acetic acid of monohaloalkanoylferrocenes. The catalyst is based on $PtO_2$. A crude synthetic product is thus obtained, with a purity generally in the region of 95%, which in particular does not require subsequent purification in order to be used as an intermediate in the synthesis of ferrocene combustion catalysts for propellants.

However, for this to be the case, it is necessary, as is shown in the Examples, to use a recrystallized, and thus very pure, starting haloalkanoylferrocene. Moreover, it turns out in practice that a purity of 95% is limiting for the abovementioned use and that it is preferable to use a haloalkylferrocene with a purity in the region of 98%. Moreover, the platinum-based catalyst is fairly expensive and hydrogenation under pressure requires relatively expensive specific equipment.

French Patent FR 2,667,600 describes the production, according to the abovementioned "Friedel-Crafts" method, of a crude synthetic haloalkanoylferrocene derivative, having a purity generally in the region of 95%, by a combination of very precise operating conditions, in particular as regards the temperature, the concentration and the amount of the reactants. The crude product thus obtained is, however, insufficiently pure to be used directly, without purification, in the abovementioned process described in French Patent FR 2,667,318. Such a use would lead, in fact, to a crude haloalkylferrocene derivative with a purity markedly less than 95% which cannot be used as is without prior purification in carrying out the subsequent stages.

French Patent FR 2,667,600 certainly mentions that the addition of a cerous salt makes it possible to obtain a crude product with a purity greater than 95%, but this addition has virtually no influence on the content of 1,1'-di(haloalkanoyl)ferrocene derivative, which remains excessively high.

A person skilled in the art knows, moreover, that it it possible chemically to reduce ferrocene ketones, especially acetylferrocene, to the corresponding alkylferrocenes, for example with the $NaBH_4/AlCl_3$ couple or with the $AlLiH_4/AlCl_3$ couple, as described by K. Schlögl, A. Mohar and M. Peterlik in Monatsch. Chem., 1961, No. 92, pp. 921–926. A person skilled in the art, however, also knows that these methods are not selective and that they also make it possible to reduce haloalkyl derivatives to the corresponding alkanes, as described, for example, by J. March in Advanced Organic Chemistry: Reactions, Mechanisms, and Structure, Second Edition, 1977, pages 399–401, which dissuades him from using them for the selective reduction of the ketone functional group of a haloalkanoylferrocene.

The present invention proposes a solution to the abovementioned problems. The subject of the invention is a simple and inexpensive process for producing haloalkylferrocenes, implemented starting with ferrocene or an alkylferrocene and a carboxylic acid halide or anhydride, in two reaction stages carried out successively in the same medium (so-called "one pot" process), the first stage being a reaction of "Friedel-Crafts" type and the second a reduction stage with a metal hydride added directly to the reaction mixture on completion of the first stage, without any prior treatment of the reaction mixture, in particular without hydrolysis of the mixture, and without any purification or isolation of the intermediate compound, as was the case previously, whereas all the corresponding unit operations (hydrolysis, extractions with problematic separations, evaporations, recrystallizations, and the like) are lengthy and expensive.

This way of carrying out the reaction, which is particularly advantageous at the industrial stage as a result of its simplicity and its low cost, also makes possible an improvement in the yield owing to the fact that the intermediate haloalkanoylferrocene derivative, which has little stability and which degrades with time, the more rapidly the more impure it is, is not isolated.

This way of carrying out the reaction is particularly surprising for several reasons. First of all, in a multistage process, a person skilled in the art regards it as important to control the purity from the first stage. Now, according to the invention, the haloalkanoylferrocene intermediate is neither purified nor isolated.

Moreover, only the choice of a metal hydride as reducing agent makes it possible to obtain this result and, unexpectedly, it is not necessary to add, with the hydride, an activator of this hydride, such as $AlCl_3$ or $BF_3$, in order to carry out the second reduction stage, while virtually all the aluminum chloride used during the first stage has been consumed by the reaction of "Friedel-Crafts" type.

Furthermore, a person skilled in the art does not observe under these conditions, and in contrast to what could be assumed from the state of the art, significant reduction of the halide functional group.

It is possible, without the Applicant company being bound by this hypothesis, that according to the invention, as a result of the absence of hydrolysis before the second reduction stage, it is not the haloalkanoylferrocene derivative which is reduced but its complex with $AlCl_3$, the result of the "Friedel-Crafts" reaction.

This fundamental difference at the level of the reactions carried out could partly be the cause of the abovementioned unexpected observations but it is nevertheless not possible, even with a posteriori reasoning based on this hypothesis, to explain them satisfactorily.

The subject of the present invention is more precisely a new process for the synthesis of haloalkylferrocenes, the said process comprising a first reaction stage of "Friedel-Crafts" type, carried out in the presence of aluminum chloride as catalyst and in organic solvent medium, which consists in reacting a carboxylic acid halide or anhydride with a ferrocene derivative chosen from the group consisting of ferrocene and alkylferrocenes. This new process is characterized in that, after this first reaction stage, without first isolating the intermediate compound and without any prior treatment of the reaction mixture, especially hydrolysis treatment, a metal hydride is added to the reaction mixture.

The haloalkylferrocenes preferably correspond to the general formula (I)

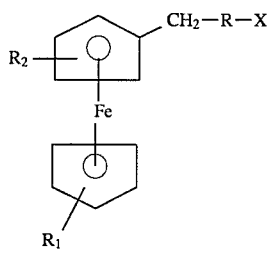

in which

R represents an alkyl chain containing 1 to 47 carbon atoms, preferably 1 to 23 carbon atoms and better still 1 to 17, 1 to 11 or even 1 to 7 and 2 to 7 carbon atoms. In a particularly preferred way, R represents $CH_2$ or a polymethylene group $(CH_2)_n$ in which n is an integer such that $2 \leq n \leq 7$.

$R_1$ and $R_2$, which are identical or different, represent hydrogen or an alkyl chain containing 1 to 8 carbon atoms and preferably 1 to 4 carbon atoms. In a particularly preferred way, $R_1$ and $R_2$ represent hydrogen or alternatively $R_1$ and $R_2$ represent the ethyl group or alternatively $R_1$ represents the ethyl group and $R_2$ hydrogen.

X represents chlorine or bromine and preferably chlorine.

According to this preferred variant in which the haloalkylferrocenes correspond to the abovementioned formula (I), on the one hand the ferrocene derivative chosen from the group consisting of ferrocene and alkylferrocenes corresponds to the general formula (II)

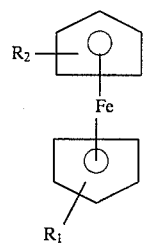

in which $R_1$ and $R_2$ have the abovementioned meaning, and, on the other hand, the carboxylic acid corresponds to the general formula X-R-COOH (III), in which X and R have the abovementioned meaning.

According to a particularly preferred variant of the invention, $R_1$ and $R_2$ represent hydrogen, X represents chlorine and n is equal to 3, that is to say that the haloalkylferrocene obtained is 4-chlorobutylferrocene.

The first reaction stage of "Friedel-Crafts" type of the process according to the invention is well known to a person skilled in the art.

Use is preferably made, as reactant, of a carboxylic acid chloride and, as solvent, of $CH_2Cl_2$. The other solvents commonly used for this type of reaction are also suitable.

Mention may be made, for example, of chlorinated solvents such as dichloroethane and chloroform.

This first reaction stage is generally carried out at a temperature of between 0° C. and 35° C.

The molar ratio of the carboxylic acid halide or anhydride to the ferrocene derivative chosen from the group consisting of ferrocene and the alkylferrocenes is preferably between 1.0 and 1.1 and the molar ratio of $AlCl_3$ to the same ferrocene derivative is between 1.0 and 1.1.

A preferred variant consists in preparing an acylating solution obtained by mixing the carboxylic acid halide or anhydride with $AlCl_3$ in the organic solvent and in then slowly pouring this acylating solution into a solution of the ferrocene derivative.

On conclusion of this first reaction, a metal hydride is added to the reaction mixture, without it being necessary to first carry out any physical or chemical treatment of this reaction mixture.

Mention may be made, as examples of metal hydrides, of $LiAlH_4$, $NaAlH_4$, $NaBH_4$, $B_2H_6$, triphenyltin hydride and $LiBH(C_2H_5)_3$.

A borohydride and more particularly $NaBH_4$, is preferably used.

According to a preferred variant, the metal hydride is added to the reaction mixture in solution in an organic solvent, preferably slowly, for example over 1 to 4 hours.

Many organic solvents are suitable, such as triglyme, diglyme, tetrahydrofuran and alkyl ethers. A solvent which is miscible with the solvent of the reaction mixture in which the first stage of "Friedel-Crafts" type has been carried out is preferably chosen.

Triglyme, of formula $CH_3—[O—(CH_2)_2—]_3OCH_3$, is particularly preferred. In fact, unexpectedly, it has been observed that the residual ferrocene was entrained with the triglyme during the subsequent isolation stage of the product by successive distillations and that there was thus no deposition of ferrocene on the traps and pipework of the plant. This result, which is not observed with other solvents, in particular with the abovementioned conventional solvents, is particularly advantageous. It makes possible, first of all, easy subsequent distillation of the haloalkylferrocene, without it being necessary first to carry out a purification by column chromatography, but also makes it possible to minimize the formation of the disubstituted derivative, whose presence, as already mentioned above, is crippling in the final ferrocenic polymer, by varying the reactant ratios in the first stage of "Friedel-Crafts" type.

In fact, as the presence of residual ferrocene no longer poses a problem in this case, it is possible to increase the molar proportion of ferrocene with respect to the carboxylic acid halide or anhydride, which decreases the risks of formation of the 1,1'-di(haloalkanoyl) ferrocene derivative.

Moreover, it has been observed that $NaBH_4$ was almost three times more soluble in triglyme than in diglyme, a solvent which is much used in the state of the art for carrying out reductions with $NaBH_4$.

This leads to a significant reduction in the volume required of a fairly expensive solvent and to a saving in time during the stage of evaporation of this solvent and, moreover, the price of triglyme is currently much less than that of diglyme.

The second reduction stage with the metal hydride is preferably carried out at a temperature of between $-10°$ C. and $10°$ C.

After this second reduction stage, in order to isolate the desired haloalkylferrocene derivative formed from the reaction mixture, it is possible, for example, to first of all hydrolyse the reaction mixture. After separation by settling, the organic phase is recovered, the organic solvent(s) is/are driven off by distillation, optionally at reduced pressure, depending on the nature of these solvents, and the haloalkylferrocene is then distilled at reduced pressure.

Other methods of isolating the desired product can be used, in particular for high mass haloalkylferrocenes, for example techniques for separation by column chromatography.

The following non-limiting examples illustrate the invention and the advantages which it provides.

EXAMPLE 1

Synthesis of 4-Chlorobutylferrocene

A) Preparation of the $AlCl_3$/4-Chlorobutyroyl Chloride Complex 5.4 l of $CH_2Cl_2$ and then 750 g of $AlCl_3$ (5.62 mol) are introduced into an enamelled reactor.

Cooling is carried out to a temperature of less than or equal to 5° C. and then 800 g of 4-chloro-n-butyroyl chloride (5.68 mol) are introduced slowly (approximately 2 h) with stirring, the reactor being cooled so that the temperature does not exceed 5° C. Stirring is continued for approximately 1 h. The acylating solution obtained (solution A) is stored at 5° C.

B) Preparation of a Solution of $NaBH_4$ in Triglyme 216 g of $NaBH_4$ (5.68 mol) are dissolved, with stirring, in 1.5 l of triglyme in a reactor. During dissolution, the temperature rises to approximately 35° C. Stirring is carried out for 2 to 3 h in order to complete the dissolution and cooling is then carried out to 25° C. (solution B).

C) Synthesis of 4-Chlorobutylferrocene 2.6 l of $CH_2Cl_2$ and then 1000 g (5.37 mol) of ferrocene are introduced into an enamelled reactor. Heating is carried out to reflux and then 0.8 to 1 l of $CH_2Cl_2$ are distilled, without exceeding 40° C., in order to free the medium of water which may have been introduced therein by the ferrocene.

While maintaining the reflux with gentle heating, the previously prepared solution A of the $AlCl_3$/4-chlorobutyroyl chloride complex is slowly run in (8 to 10 h).

The reaction mixture is then left for 30 min at reflux and is then cooled to −5° C.

A purple solution is obtained into which the previously prepared solution B of $NaBH_4$ in triglyme is progressively run (2 to 3 h), while maintaining the temperature at less than or equal to −5° C.

The reaction mixture takes on an orangey appearance.

The reaction mixture is left stirring for approximately 1 h at 0° C.

The mixture is then hydrolysed (6 l of water) while maintaining its temperature at less than or equal to 10° C. The mixture is allowed to separate by settling and the organic phase is then withdrawn.

The aqueous phase is washed with 3 times 1 l of $CH_2Cl_2$ and then all the organic phases are combined, that is to say the organic phase resulting from the reaction mixture and the 3 organic phases from washing the aqueous phase.

The combined organic phases are then washed with 1.5 l of water saturated with NaCl and then, at atmospheric pressure, $CH_2Cl_2$ is distilled by heating the combined and washed organic phases to a pot temperature of approximately 80° C. 7 to 8 l of $CH_2Cl_2$ are thus recovered which can be recycled after drying over $Na_2SO_4$. The residual $CH_2Cl_2$ is then extracted at approximately 80° C. and at reduced pressure, approximately 100 mm Hg ($1.33 \times 10^4$ Pa).

The triglyme and the residual ferrocene which is found to be entrained by the triglyme are then distilled at reduced pressure, approximately 15 mm Hg ($2 \times 10^3$ Pa) and at a column head temperature of 80°–90° C.

There are then distilled, at a still more reduced pressure, less than 3 mm Hg ($4 \times 10^2$ Pa) and at a temperature of between 147° and 155° C., 1160 g of 4-chlorobutylferrocene, identified by elemental analysis and by proton NMR spectrometry and IR spectrometry. The yield is 78% with respect to the starting ferrocene.

The purity of the 4-chlorobutylferrocene obtained is greater than 99%.

Analysis by gas phase chromatography indicates that it contains less than 0.2% by weight of ferrocene, less than 0.2% by weight of 1,1'-di(4-chlorobutyl)ferrocene, less than 0.1% by weight of butylferrocene, less than 0.1% by weight of 4-hydroxybutylferrocene and approximately 0.4% by weight of triglyme.

EXAMPLE 2

Synthesis of 3-Chloropropylferrocene

The process of synthesis is identical to that of Example 1, except that 720 g of 3-chloro-n-propionyl chloride (5.66 mol) are used in place of 800 g of 4-chloro-n-butyroyl chloride.

3-Chloropropylferrocene is obtained by distillation at reduced pressure, approximately 1 mm Hg ($1.5 \times 10^2$ Pa), at a temperature of between 110° C. and 112° C.

3-Chloropropylferrocene, identified by proton NMR spectrometry and IR spectrometry, is obtained with a yield of 70% with respect to the starting ferrocene.

Chromatographic analysis shows that its purity is greater than 99%.

We claim:

1. In a process for the synthesis of haloalkylferrocenes, comprising a first stage of reaction, in the presence of aluminum chloride as catalyst and in organic solvent medium, of a haloalkyl carboxylic acid halide or haloalkyl carboxylic acid anhydride with a ferrocene derivative chosen from the group consisting of ferrocene and alkylferrocenes to produce an intermediate compound which is thereafter reduced to provide the haloalkylferrocene, the improvement wherein, after this first reaction stage, without first isolating the intermediate compound, a metal hydride is added to the reaction mixture to reduce said intermediate compound.

2. Synthetic process according to claim 1, characterized in that the haloalkylferrocenes correspond to the general formula (I)

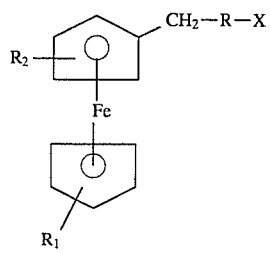

in which

R represents an alkyl chain containing 1 to 47 carbon atoms, $R_1$ and $R_2$, which are identical or different, represent hydrogen or an alkyl chain containing 1 to 8 carbon atoms, X represents chlorine or bromine, in that the ferrocene derivative chosen from the group consisting of ferrocene and alkylferrocenes corresponds to the general formula (II)

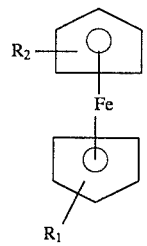

in which $R_1$ and $R_2$ have the abovementioned meaning, and in that the carboxylic acid corresponds to the general formula X-R-COOH (III) in which X and R have the abovementioned meaning.

3. Synthetic process according to claim 2, characterized in that R represents $CH_2$ or a polymethylene group $(CH_2)_n$ in which n is an integer such that $2 \leq n \leq 7$.

4. Synthetic process according to claim 3, characterized in that $R_1$ and $R_2$ represent hydrogen, X represents chlorine and n is equal to 3.

5. Synthetic process according to claim 1, characterized in that the metal hydride is a borohydride.

6. Synthetic process according to claim 5, characterized in that the borohydride is sodium borohydride.

7. Synthetic process according to claim 1, characterized in that the metal hydride is added to the reaction mixture in solution in an organic solvent.

8. Synthetic process according to claim 7, characterized in that the metal hydride is in solution in triglyme.

9. Synthetic process according to claim 1, characterized in that the first stage is carried out in methylene chloride medium.

10. Synthetic process according to claim 1, characterized in that, after the addition of the metal hydride, the reaction mixture is hydrolysed and the organic phase is recovered and then in that the haloalkylferrocene is isolated by distillation of the organic phase.

* * * * *